United States Patent [19]
Hamill et al.

[11] Patent Number: 4,876,273
[45] Date of Patent: Oct. 24, 1989

[54] ANTIBOTIC A80577 AND PROCESS FOR ITS PRODUCTION

[75] Inventors: Robert L. Hamill, Greenwood; Raymond C. Yao, Carmel, both of Ind.

[73] Assignee: Eli Lilly and Company, Indianapolis, Ind.

[21] Appl. No.: 220,650

[22] Filed: Jul. 18, 1988

Related U.S. Application Data

[63] Continuation-in-part of Ser. No. 85,039, Aug. 13, 1987, abandoned.

[51] Int. Cl.$^4$ .................. A61K 31/35; A61K 31/365; C07D 309/06
[52] U.S. Cl. ................................. 514/451; 549/414; 549/315; 549/317
[58] Field of Search ................ 514/451; 549/414, 315, 549/317

[56] References Cited
U.S. PATENT DOCUMENTS 3,839,557 10/1974 Raun ..................................... 424/115
4,279,894 7/1981 Davies et al. ........................ 424/122
4,443,471 4/1984 Davies et al. ........................ 424/279

OTHER PUBLICATIONS

Davies et al., "Structure of Antibotic M139603; X-ray Crystal Structure of the 4-Bromo-3,5-dinitrobenzoyl Derivative", *J. Chem. Comm.*, 1073 (1981).
Keller–Juslen et al., "Tetronomycin, a Novel Polyether of Unusual Structure", *J. Antibiotics*, 142–150 (1982).

*Primary Examiner*—Nicky Chan
*Attorney, Agent, or Firm*—Mary Ann Tucker; Leroy Whitaker

[57] ABSTRACT

New polyether antibiotic A80577, its acyl ester and alkyl ether derivatives, and salts thereof, are useful antibacterial agents and increase feed-utilization efficiency in animals. Methods of making A80577 by culture of *Actinomadura verrucosospora*, NRRL 18236, and compositions containing an A80577 compound also are provided.

13 Claims, 2 Drawing Sheets

ANTIBOTIC A80577 AND PROCESS FOR ITS PRODUCTION

CROSS-REFERENCE TO RELATED APPLICATION

This application is a continuation-in-part of application Ser. No. 07/085,039, filed Aug. 13, 1987 now abandoned.

SUMMARY OF THE INVENTION

This invention relates to the new polyether antibiotic A80577 and to a new strain of *Actinoma verrucosospora*, NRRL 18236, which produces this antibiotic. The structure of A80577 is shown in formula 1:

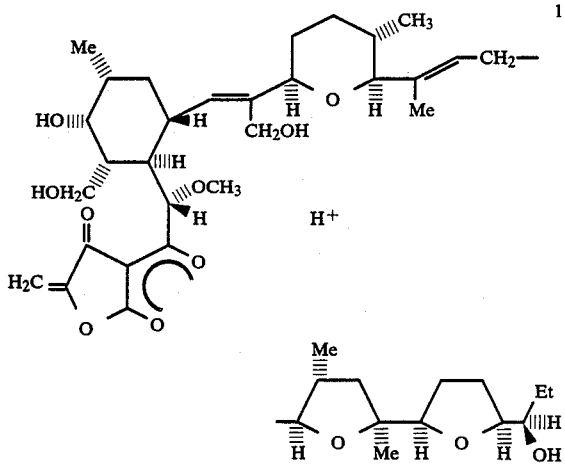

This invention also relates to acyl ester and alkyl ether derivatives of A80577 and to the salts of A80577 and of the derivatives.

Another aspect of this invention is a process for producing A80577 by cultivating *Actinomadura verrucosospora*, NRRL 18236, under submerged aerobic fermentation conditions until a substantial level of the antibiotic is produced. A80577 is extracted from the fermentation broth and from the mycelium with organic solvents. A80577 is separated and further purified by techniques such as column chromatography.

Because *Actinomadura verrucosospora*, NRRL 18236, is a newly discovered strain, this invention further provides a biologically pure culture of this microorganism.

A80577 is a useful antibacterial agent. It improves feed-utilization efficiency in ruminants and acts as a growth promotant in ruminants and in monogastric animals. In addition, A80577 has parasiticidal activity and is useful as an ionophore. Methods and compositions pertaining to these uses are also provided.

DESCRIPTION OF THE DRAWINGS

The drawings show the following infrared absorption spectra in chloroform.

DETAILED DESCRIPTION OF THE INVENTION

Improved antibiotics continue to be needed in the veterinary field. Enhancing growth promotion in animals is one desired feature of such antibiotics. Growth promotion can be achieved by reducing disease and by increasing feed-utilization efficiency. Of particular interest is growth promotion in ruminants, such as cattle.

The mechanism for utilizing the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA).

The relative efficiency of VFA utilization is connected to overall efficiency. Thus, although acetates and butyrates are used, propionates are used with greater efficiency. Also, the fermentation efficiency of propionate production is greater than that of butyrate or acetate. This is in addition to the utilization efficiency. A beneficial compound, therefore, stimulates animals to produce a higher proportion of propionates from carbohydrates, thereby increasing carbohydrate-utilization efficiency.

A80577 is a new member of the group of polyether antibiotics. Westley (John W. Westley, "Polyether Antibiotics: Naturally Occurring Acid Ionophores, Vol. 2, Chemistry," Marcel Dekker, New York, 1983; *Journal of Natural Products*, 49(1), 35 [1986]) has separated existing polyethers by class and type. Using Westley's system, A80577 is a new member of the Class 4 group of polyethers. This group includes tetronomycin, which is described in *J. Antibiotics*, 142 (1982), and M139603, which is described in *J. Chem. Soc., Chem. Comm.*, 1073 (1981) and U.S. Pat. No. 4,279,849.

Characteristics of A80577

A80577 (in its sodium salt form) has the following characteristics:
State: white crystals (from acetone-water)
mp:
 (Na Salt) 276°–278° C.
 (K Salt) 270°–272° C.
Molecular weight: 782 by field desorption mass spectrometry (FDMS); 760 for acid form.
$[\alpha]^{25}D$: −89.03 (c 5, MeOH)
No titratable groups (66% DMF)
Empirical formula: $C_{42}H_{63}O_{12}Na$
UV max: Ethanol neutral 253 nm ($\epsilon=17,735$), 298 nm

| | | |
|---|---|---|
| acidic | 250 nm | ($\epsilon = 10,003$) ($\epsilon = 14,715$), 289 nm ($\epsilon = 7,971$) |
| basic | 208 nm | ($\epsilon = 192,222$), 248 nm ($\epsilon = 15,968$), 286 nm ($\epsilon = 9,665$) |

Figure 1:
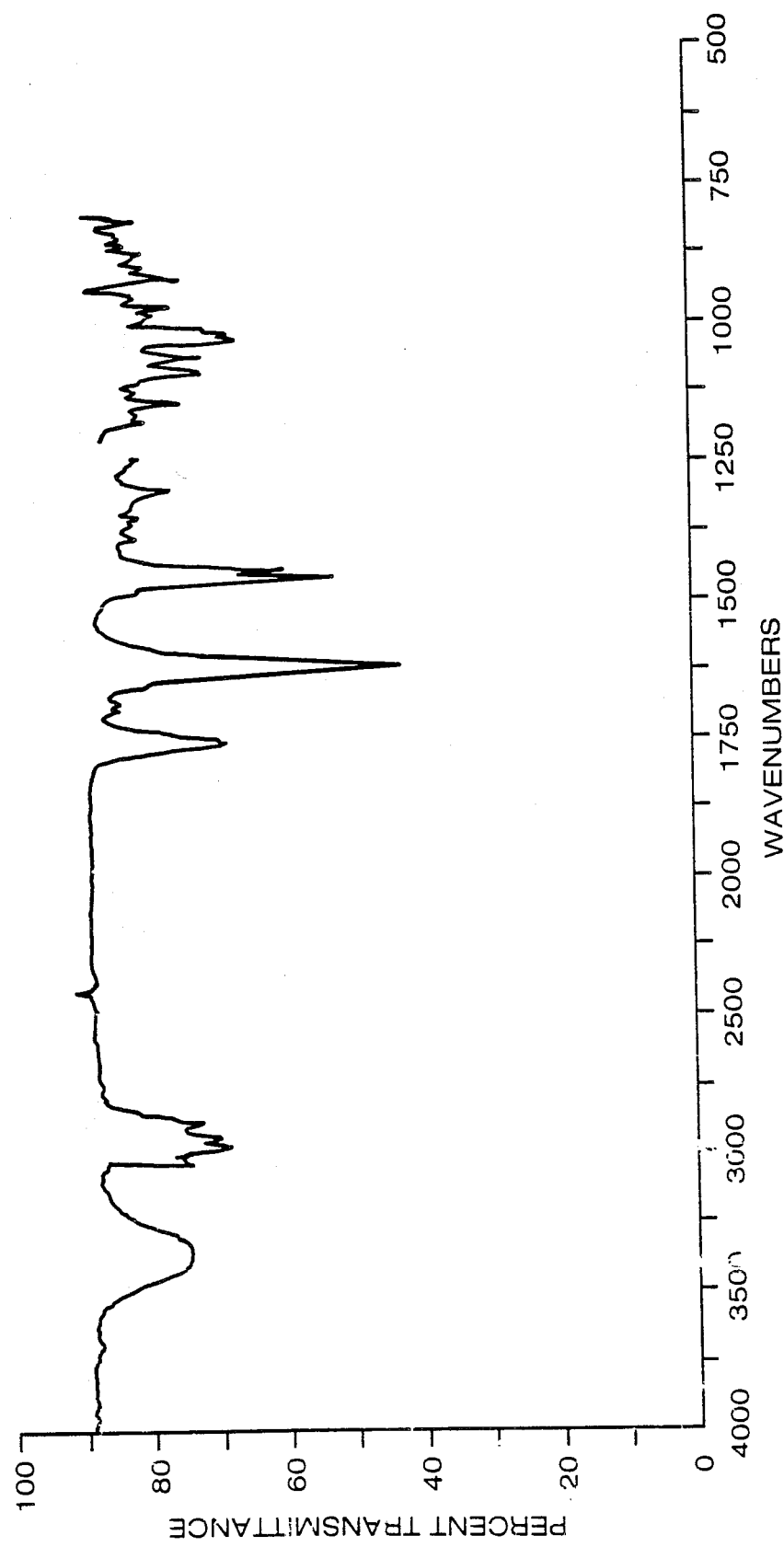
FIG. 1: A80577 (Na Salt)
Figure 2:
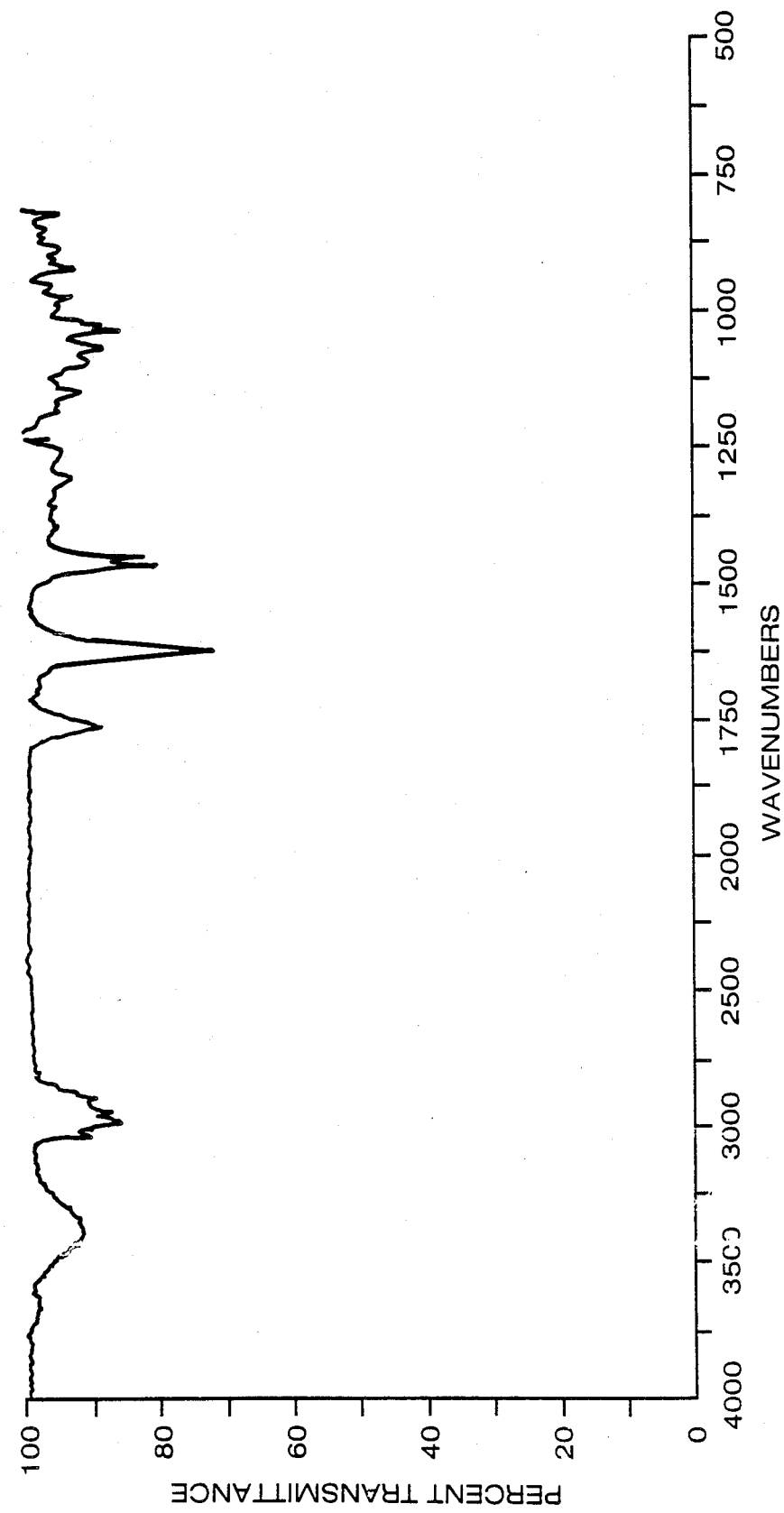
FIG. 2: A80577 (K Salt)

IR (Na salt, $CHCl_3$): 3018, 2966, 2931, 1750, 1611, 1453, 1439, 1219, 1022 and 1012 cm$^{-1}$ (see FIG. 1)
IR (K salt, $CHCl_3$): 3023, 3019, 2967, 2964, 2930, 2874, 1750, 1650, 1650, 1451, 1437, 1224, 1214, 1210, 1079, 1059, 1022 and 1012 cm$^{-1}$ (see FIG. 2)
Solubility: Not very soluble in water; soluble in dimethyl sulfoxide, dimethylformamide, lower alcohols such as methanol, ketones such as acetone, esters such as ethyl acetate, halogenated hydrocarbons such as chloroform and hydrocarbons such as diethyl ether, benezene, toluene and warm hexane.

Based on its physical characteristics A80577 is believed to have the structure shown in formula 1. As is apparent from its structure, A80577 is a charged molecule and is capable of forming salts. A80577 also has up to four hydroxyl groups which can be esterified or which can form ether derivatives. The acyl ester and the alkyl ether derivatives of A80577, and the pharmaceutically-acceptable salts of A80577 and of these derivatives are also useful as antibiotics and as agents which increase feed-utilization efficiency. The term "an A80577 compound" is used herein to designate antibiotic A80577 (formula 1), an acyl ester or an alkyl ether derivative of antibiotic A80577 or a pharmaceutically acceptable salt of antibiotic A80577 or of its acyl ester or alkyl ether derivatives.

Antibiotic A80577 is produced by a culture of an A80577-producing strain of *Actinomadura verrucosospora*, NRRL 18236, as described herein. The antibiotic is produced under submerged aerobic conditions in a suitable culture medium; it can be recovered from the culture medium by using various isolation and purification procedures understood in the art.

A culture of the A80577-producing organism has been deposited and made part of the stock culture collection of the Midwest Area Northern Regional Research Center, Agricultural Research Service, U.S. Department of Agriculture, 1815 North University Street, Peoria, Illinois 61604, from which it is available to the public under the accession number NRRL 18236.

Taxonomic studies of this organism were carried out by Frederick P. Mertz of the Lilly Research Laboratories. Based on these studies and comparison with the published descriptions of other species, the organism is classified as a strain of *Actinomadura verrucosospora* [Lechevalier and Lechevalier, Chemical composition as a criterion in the classification of aerobic actinomyces, Int. J. Syst. Bacteriol., 20:435–43; H. Nonomura and Y. Ohara, Distribution of Actinomycetes in Soil. (X1) Some new species of the genus *Actinomadura*. Lechevalier et al., J. Ferm. Tech. 49:904–912 (1971); M. Athalye, M. Goodfellow, J. Lacey, and R. P. White, Numerical classification of *Actinomadura* and *Nocardiopsis*. Int. J. Syst. Bacteriol. 35:86–98 (1985); M. Goodfellow and G. Alderson, Numerical taxonomy of Actinomadura and related actinomycetes. J. Gen. Microbiol. 112:95–111 (1979); V. B. D. Skerman, V. McGowan, and P. H. A. Sneath (ed.), Approved Lists of Bacterial Names. Int. J. Syst. Bacteriol. 30:225–420 (1980)].

Methods Used

The methods recommended by the International Streptomyces Project (ISP) for the characterization of Streptomyces species [E. B. Shirling and D. Gottlieb, "Methods for Characterization of Streptomyces Species", *Int. J. Syst. Bacteriol.* 16(3), 313–340 (1966)] have been followed.

Melanoid pigment production (chromogenicity) was determined with ISP No. 1 (tryptone-yeast extract broth), ISP No. 6 (peptone-yeast extract iron agar), and ISP No. 7 (tyrosine agar).

Starch hydrolysis was determined by testing for the presence of starch with iodine on ISP No. 4 (inorganic salts-starch agar) plates.

Morphology was studied using an optical light microscope. A scanning electron microscope (SEM) was used to study the spore surface ornamentation.

ICSS-NBS Centroid Color Charts, standard sample No. 2106 (National Bureau of Standards, 1958, U. S. Department of Commerce, Washington, D.C.) and the Color Harmony Manual (4th ed., Color Standards Department, Container Corporation of America, Chicago Ill., 1958) were used to assign color names to the reverse side and aerial spore mass respectively.

The isomers of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between *Nocardia* and *Streptomyces* by Paper Chromatography of Whole-cell Hydrolysates", *Appl. Microbiol.* 12, 421–423 (1964)] and of Lechevalier [M. P. Lechevalier, and H. Lechevalier, "Chemical Composition as a Criterion in the Classification of Aerobic Actinomycetes", *Int. J. Syst. Bacteriol.* 20, 435–443 (1970)].

Resistance to antibiotics was measured by padding antibiotic sensitivity discs onto the surface of seeded ISP No. 2 agar plates.

Cultural Characteristics

Culture A80577 grew well on both complex and defined media. The aerial spore mass was moderately formed, and was white. The reverse side was yellowish white to pale yellow. No distinctive pigments were observed. No soluble pigments were observed, except for a light yellow brown pigment in several media. These cultural characteristics are given in Table I.

TABLE I

Cultural Characteristics of A80577 at 30° C. 18 days incubation

| | | | | |
|---|---|---|---|---|
| ISP No. 2 | G: Abundant<br>R: 88.d.Y<br>C: Trace: a White<br>Sp: None to 1.y Br | Czapek's | G: Fair<br>R: 92.y White<br>Am: Fair: a White<br>Sp: None |
| ISP No. 3 | G: Fair<br>R: 92.y White<br>Am: Fair: a White<br>Sp: None | Tomato Paste Oatmeal Agar | G: Poor<br>R: 88.d.Y<br>Am: Poor: a White<br>Sp: None |
| ISP No. 4 | G: Good<br>R: 92.y White<br>Am: Good a White<br>Sp: None | Potato Carrot Agar | G: Good<br>R: 89.p.Y<br>Am: Good: a White<br>Sp: None |
| ISP No. 5 | G: Abundant<br>R: 89.p.Y<br>Am: Good: a White<br>Sp: None | Jensen's Agar | G: Poor<br>R: 92.y White<br>Am: Poor: a White<br>Sp: None |
| ISP No. 7 | G: Good<br>R: 90.gy.Y<br>Am: None | Glucose Asparagine | G: Good<br>R: 89.p.Y<br>Am: Good: a White |
| No. 172 | Sp: None<br>G: Good<br>R: 89.p.Y<br>Am: Good: a White<br>Sp: None | Glycerol Glycine | Sp: None<br>G: Trace only<br>R: —<br>Am: —<br>Sp: — |
| Tap Water Agar | G: Not grown<br>R: —<br>Am: —<br>Sp: — | Yeast Dextrose Agar | G: Abundant<br>R: 87.m.Y<br>Am: Fair: a White<br>Sp: None to 1.yBr |

G: Abundant
Emerson's R: 87.m.Y
agar Am: Trace: a White
SP: None to 1.yBr
G = Growth;
R = Reverse;
Am = Aerial mycelium;
Sp = Soluble Pigment

Morphological Characteristics

Culture A80577 produces an extensive substrate mycelium. Moderately formed aerial hyphae produce clusters of tightly packed short chains, arranged in Rectusflexibilis (RF) morphology. This morphology is typical of the genus *Actinomadura*. The spore shape is spherical, spore size averages 0.8 μm, and the spore surface has a distinctive granular appearance. The spore chain contains less than 10 spores per chain.

Physiological Characteristics

Analysis of hydrolyzed whole cells indicates the presence of maso-diaminopimelic acid. Madurose was detected in the whole cell extracts. Galactose, glucose, mannose and ribose were also detected. The cell wall is type III and the sugar pattern is type B. Galactose is not typical of type B sugar pattern.

Culture A80577 utilized the following carbohydrates: adonitol, D and L-arabinose, cellobiose, dulcitol, ethanol, i-erythritol, D-fructose, D-galactose, glucose, glycerol, glycogen, i-inositol, D-mannitol, D-mannose, D-melizitose, D-melibiose, L-rhamnose. D-ribose, sucrose, D-trehalose D-xylose and sodium butyrate. It was unable to utilize: cellulose, dextrin, inulin, D-lactose, D-maltose, a-methyl-D-glucoside, D-raffinose, salicin, sorbitol, L-sorbose, and xylitol. Control plates with no carbohydrates supported a minimal growth.

Culture A80577 grew in a temperature range of 15°–45° C. optimum growth appeared to be between 30 and 37° C. A80577 tolerated up to 4% NaCl, produced catalase and reduced nitrates. It did not hydrolyze starch.

A80577 was resistant to: bacitracin 10 units, cephalothin 30 μg, lincomycin 2 μg, oleandomycin 15 μg, penicillin G 10 units, rifampin 5 μg, and tetracycline 30 μg. It was sensitive to: gentamicin 10 μg, neomycin 30 μg, streptomycin 10 μg, tobramycin 10 μg and vancomycin 30 μg.

Identity of Strain A80577

The chemotaxonomic properties and the general cultural and morphological characteristics of A80577 support the assignment of this strain to the genus Actinomadura. Comparison of A80577 to the published descriptions of other Actinomadura species indicated a close similarity to *A. verrucosospora*. Table II lists these comparisons.

TABLE II

Comparison of A80577 and *A. verrucosospora*

|  | A80577 | A. verrucosospora |
|---|---|---|
| Cultural characteristics: | | |
| aerial hyphae moderate | + | + |
| aerial color white | + | + |
| diffusible pigment | + | + |
| Biochemical characteristics: | | |
| allantoinase production | − | − |
| melanin production | − | − |
| nitrate reduction | + | + |
| urease production | − | − |
| Degradation of: | | |
| adenine | − | − |
| aesculin | + | + |
| casein | + | + |
| elastin | + | + |
| gelatin | + | + |
| guanine | − | − |
| hypoxanthine | + | + |
| starch | − | − |
| testosterone | + | + |
| tyrosine | − | + |
| xanthine | − | − |
| Growth on sole carbon source (1% w/v): | | |
| adonitol | + | + |
| D-arabinose | − | − |
| L-arabinose | + | + |

TABLE II-continued

Comparison of A80577 and *A. verrucosospora*

|  | A80577 | A. verrucosospora |
|---|---|---|
| cellobiose | + | + |
| dextrin | − | + |
| dulcitol | − | − |
| erythritol | − | − |
| ethanol | − | − |
| fructose | + | + |
| galactose | + | + |
| glucose | + | + |
| glycerol | + | + |
| glycogen | − | + |
| inositol | + | − |
| inulin | − | − |
| lactose | + | + |
| maltose | + | + |
| mannitol | + | + |
| mannose | + | − |
| melezitose | + | − |
| melibiose | − | − |
| a-methyl-D-glucoside | − | − |
| raffinose | − | − |
| rhamnose | + | + |
| salicin | + | − |
| sorbitol | − | − |
| sucrose | + | + |
| trehalose | + | + |
| xylose | + | + |
| Utilization of: | | |
| sodium acetate | + | − |
| sodium butyrate | + | + |
| sodium propionate | − | + |
| sodium pyruvate | + | − |
| sodium tartrate | − | − |
| Growth at: | | |
| 10° C. | − | − |
| 20° C. | + | + |
| 45° C. | + | − |
| Resistance to: | | |
| gentamycin 10 μg | − | − |
| lincomycin 2 μg | + | + |
| neomycin 30 μg | − | − |
| oleandomycin 15 μg | − | + |
| penicillin 10 i.u. | + | + |
| tobramycin 10 μg | − | + |

+ = characteristic present
− = characteristic absent

Although A80577 does not match identically the properties of *A. verrucosospora*, it has a great similarity in cultural characteristics. Therefore, culture A80577 is classified as a strain of *Actinomadura verrucosospora* Nonomura and Ohara 1971. *Actinomadura verrucosospora* is listed in the Approved List of Bacterial Names [V. B. D. Skerman, V. McGowan and P. H. A. Sneath, Eds., *Int. J. Syst. Bacteriol.* 30, 225–420 (1980)] and is a validly published species.

As is the case with other organisms, the characteristics of the A80577-producing culture *Actinomadura verrucosospora*, NRRL 18236, are subject to variation. Recombinants, mutants or variants of the strain may be obtained by methods known in the art. For example, mutants can be obtained by treatment with various known physical and chemical mutagens such as ultraviolet light, X rays, gamma rays and chemicals such as N-methyl-N′-nitro-N-nitrosoguanidine. All natural and induced variants, mutants and recombinants of this *Actinomadura verrucosospora*. strain which retain the characteristic of A80577 production are part of this invention.

The culture medium used to grow *Actinomadura verrucosospora*, NRRL 18236, can be any one of a number of media. For economy in production, optimal yield, and ease of product isolation, however, certain culture media are preferred. For example, a preferred carbohydrate source in large-scale fermentation is glucose, although blackstrap molasses, starch and the like can also be used.

A preferred nitrogen source is enzyme-hydrolyzed case in, although other nitrogen sources should also be useful.

Among the nutrient inorganic salts which may advantageously be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. If foaming is a problem, small amounts (i.e. 0.2 ml/L) of an antifoam agent such as polypropylene glycol may be added to large scale fermentation media if needed.

For production of substantial quantities of antibiotic A80577, submerged aerobic fermentation in tanks is preferred. Small quantities of A80577 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A80577 is produced by *Actinomadura verrucosospora*, when grown at temperatures between about 25° and about 37° C. A good temperature for A80577 production appears to be about 30° C.

As is customary in submerged aerobic culture processes, sterile air is blown into the vessel from the bottom while the medium is stirred with conventional turbine impellors. In general, the aeration rate and agitation rate should be sufficient to maintain the level of dissolved oxygen at or above 30% of saturation.

Production of antibiotic A80577 can be followed during the fermentation by testing samples of the broth for antibiotic activity against organisms known to be sensitive to the antibiotic. One assay organism useful in testing A80577 is *Bacillus subtilis* ATCC 6633. The bio-assay is conveniently performed by the agar-well plate test.

Following its production under submerged aerobic fermentation conditions, A80577 can be recovered from the fermentation medium by methods used in the fermentation art. The antibiotic activity produced during fermentation of the A80577-producing organism occurs both in the mycelia and the broth. Maximum recovery of A80577 is accomplished, therefore, by initially filtering the medium to separate the broth from the mycelial mass. The filtered broth and the mycelial mass can then be purified separately to give their respective portion of A80577. A variety of techniques may be used in this purification.

A preferred technique for purification of the filtered broth involves adjusting it to a pH of about 9 and extracting with a suitable solvent such as, for example, ethyl acetate. The extracting solvent can then be evaporated under vacuum to give the broth portion of A80577.

A preferred method of purifying the mycelial mass is to extract the separated mycelial filter cake with a suitable solvent such as, for example, acetone. The extracting solvent is then evaporated under vacuum to give a concentrated aqueous solution. This aqueous solution is then adjusted to a pH of about 9 and is extracted with a suitable solvent such as, for example, ethyl acetate. The extracting solvent is then concentrated under vacuum to give the mycelial portion of A80577.

The broth and mycelial portions of the A80577 complex are further purified by similar procedures. A preferred procedure involves silica gel chromatography.

Separation of antibiotic A80577 can be followed by thin-layer chromatography (TLC) or high performance liquid chromatography (HPLC). Convenient silica gel TLC solvent systems are ethyl acetate, ethyl acetate: acetonitrile: ammonium hydroxide and toluene: acetonitrile: acetic acid. Preferred silica gel solvent systems are ethyl acetate, ethyl acetate:acetonitrile: ammonia (90:9:1) and toluene:acetonitrile:acetic acid (40:59:1). Polyamide plates also may be conveniently used with an acetone:water:ammonia solvent system, preferably in the ratio 30:69:1. The antibiotic can be detected by bioautography using, for example, *Bacillus subtilis* or by other methods such as, for example, vanillin-sulfuric acid spray reagent.

Alternatively, the culture solids, including medium constituents and mycelium can be used without extraction or separation, but preferably after removal of water, as a source of A80577. For example, after production of A80577, the whole fermentation broth can be dried by lyophilization, by drum-drying, or by azeotropic distillation and drying. The dried broth is then mixed directly into feed premix.

The salts of A80577 and of its derivatives are useful for separating and purifying the antibiotics. The pharmaceutically-acceptable salts are particularly useful. Examples of salts are the alkali-metal and alkaline-earth-metal salts of A80577 and of its derivatives.

Representative and suitable alkali-metal and alkaline-earth metal salts of A80577 include the sodium, potassium, lithium, cesium, rubidium, barium, calcium and magnesium salts.

It is well known in the veterinary pharmaceutical art that the form of an antibiotic is not ordinarily of great significance when treating an animal with the antibiotic. In most cases, conditions within the animal change the drug to a form other than that in which it was administered. The salt form in which it may be administered is, therefore, not of great significance. The salt form may, however, be chosen for reasons of economy, convenience, and toxicity.

The alkali-metal and alkaline-earth-metal cationic salts of A80577 are prepared according to procedures commonly used for the preparation of cationic salts. For example, the free acid form of A80577 is dissolved in a suitable solvent such as acetone; about ½ volume of water is added and this solution is adjusted to a pH of about 9 to 10 with the base of the desired cationic salt (e.g. NaOH, KOH). The salt thus formed can be isolated by routine methods, such as filtration or evaporation of the solvent.

A preferred method of forming salts is to dissolve A80577 (acid form) in a solvent such as tetrahydrofuran; add an equal volume of water; adjust the mixture to pH 10 with the corresponding cationic base (e.g. NaOH, KOH, etc.); and extract with a water immiscible solvent such as diethyl ether or ethyl acetate. The separated organic phase is washed with water and concentrated to dryness. The residue is lyophilized from dioxane. The salt can be crystallized from an appropriate solvent, such as acetone.

The alkyl ether derivatives of A80577 are those compounds wherein one or more of the hydroxyl groups has been replaced by a YR group wherein:

Y represents O or S; and

R represents $C_1$-$C_6$-alkyl, $C_1$-$C_4$-alkoxy-$C_2$-$C_5$-alkyl, $C_1$-$C_4$-alkoxycarbonyl-$C_2$-$C_5$-alkyl, amino-$C_2$-$C_5$-alkyl, mercapto-$C_2$-$C_5$-alkyl, hydroxyalkyl, haloalkyl, or $(R')_m$-phenyl$(CH_2)_n$—, wherein R' represents $C_1$-$C_4$-alkyl, $C_1$-$C_4$-alkoxy, or hydroxy m represents 0-2; and n represents 0-3.

The term "alkyl" means a $C_1$ to $C_7$ straight or branched chain hydrocarbon, preferably a $C_1$ to $C_4$ hydrocarbon, e.g., methyl, ethyl, propyl, isopropyl, n-butyl, etc.

The term "alkoxy" means a $C_1$ to $C_7$ lower alkyl group having an oxygen function substituted therein, such as methoxy, ethoxy, propoxy and the like.

The term "hydroxyalkyl" refers either to a monohydroxy-$C_1$-$C_5$-alkyl moiety or, when Y is O, to the 2,3-dihydroxyprop-1-yl moiety.

The term "haloalkyl" refers to a $C_2$-$C_5$-alkyl moiety having from one to three halogen substituents, selected from the group consisting of bromine, chlorine, and fluorine. When the alkyl moiety is dihalo- or trihalo-substituted, the halo-substituents must be the same halogen moiety.

Preferred A80577 ether derivatives are those compounds wherein Y represents O and R represents $C_1$-$C_6$-alkyl. The ether derivatives are prepared by reacting A80577, or a salt thereof, with a corresponding primary alcohol or thiol.

With some of the starting alcohols or thiols it may be necessary to add an acid catalyst to the reaction. Suitable catalysts include hydrochloric acid, sulfuric acid, perchloric acid, methanesulfonic acid, benzenesulfonic acid, toluenesulfonic acid, selenium dioxide, and boron trifluoride.

A solvent such as, for example, water, acetone, benzene, ether, tetrahydrofuran, or dioxane may be added to facilitate the reaction. Reactions generally occur at room temperature, although higher temperatures may be used.

The acyl ester derivatives of A80577 are those compounds wherein one or more of the hydroxyl groups has been replaced by a radical of the formula

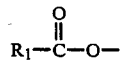

wherein $R_1$ is $C_1$ to $C_6$-alkyl or hydrogen.

A80577 acyl ester derivatives are prepared by treating A80577 with a corresponding acid anhydride or acid chloride. Esterification occurs at one of the A80577 hydroxyl groups. Such esters are typically prepared by reacting A80577 with, for example, the corresponding acid anhydride at room temperature.

Although ordinary reaction work-up procedures are sometimes sufficient, additional purification may be required to obtain the compounds of this invention. Such purification may be accomplished by well-known methods, such as, for example, column chromatography, thin-layer chromatography, fractional crystallization and the like.

The A80577 compounds inhibit the growth of bacteria which are pathogenic to animal life. For example, Table III shows the minimal inhibitory concentration (MIC) at which A80577 inhibits certain organisms. The MIC,s in Table III were determined by conventional agar-dilution assays.

TABLE III

| Antibacterial Activity of A80577 (Na salt) | |
|---|---|
| Test Organism | MIC (mcg/mL) |
| Staphylococcus aureus X1.1 | 0.5 |
| Staphylococcus aureus V41 | 0.5 |
| Staphylococcus aureus X400 | 0.5 |
| Staphylococcus aureus S13E | 0.5 |
| Staphylococcus epidermidis EPI1 | 0.5 |
| Staphylococcus epidermidis 222 | 0.5 |
| Streptococcus pyogenes C203 | 0.125 |
| Streptococcus pneumoniae Park1 | 0.125 |
| Streptococcus pneumoniae X66 | 0.5 |
| Streptococcus pneumoniae 2041 | 0.5 |
| Haemophilus influenzae | 32-128 |
| Other Gram-negative bacteria tested | >128 |
| Veterinary Organisms | |
| Staphylococcus sp. | <0.05 |
| Streptococcus sp. | <0.05 |
| Pasteurella multocida | 1.56 |
| Pasteurella hemolytica | >50 |
| Bordetella bronchiseptica | >50 |
| Mycoplasma gallisepticum | 0.78 |
| Mycoplasma hyopneumoniae | 1.56 |
| Escherichia coli | >50 |
| Salmonella typhimurium | >50 |

The A80577 compounds also are active against anaerobic bacteria. Table IV shows the MIC's at which A80577 inhibits various anaerobic bacteria, as determined by standard agar-dilution assay. End points were read after 24-hour incubation.

TABLE IV

| Susceptibility of Anaerobic Bacterial Isolates to A80577 (Na salt) | |
|---|---|
| Anaerobic Bacteria | MIC (mcg/mL) |
| Clostridium difficile 2994 | <0.5 |
| Clostridium perfringens 81 | <0.5 |
| Clostridium septicum 1128 | <0.5 |
| Eubacterium aerofaciens 1235 | <0.5 |
| Peptococcus asaccharolyticus 1302 | <0.5 |
| Peptococcus prevoti 1281 | <0.5 |
| Peptostreptococcus anaerobius 1428 | <0.5 |
| Peptostreptococcus intermedius 1624 | <0.5 |
| Propionibacterium acnes 79 | <0.5 |
| Bacteroides fragilis 111 | >128 |
| Bacteroides fragilis 1877 | >128 |
| Bacteroides fragilis 1936B | >128 |
| Bacteroides thetaiotaomicron 1438 | 4 |
| Bacteroides melaninogenicus 1856/28 | 1.0 |
| Bacteroides melaninogenicus 2736 | 16 |
| Bacteroides vulgatis 1211 | 4 |
| Bacteroides corrodens 1874 | >128 |
| Fusobacterium symbiosum 1470 | <0.5 |
| Fusobacterium necrophorum 6054A | <0.5 |

The acute toxicity of A80577 in mice, when administered by intraperitaneal injection and expressed as $LD_{50}$, was 53.3 mg/kg.

Another important property of the A80577 compounds is the ability to improve feed-utilization efficiency in animals. For example, the A80577 compounds improve feed-utilization efficiency in ruminants which have a developed rumen function.

The efficiency of feed use can be monitored by observing the production and concentration of propionate compounds in the rumen using the method described by Arthur P. Raun in U.S. Pat. No. 3,794,732 (see especially Example 5). Table V shows the effect of compound A80577 on ruminant feed-utilization efficiency. Table VA. shows the relationship between dosage of A80577 and propionate production. Table VB. shows the ratio of volatile-fatty-acid (VFA) concentrations in A80577-treated flasks to concentrations in control flasks in this test.

TABLE V

Effect of A80577 (Na Salt) on Ruminant Feed-Utilization Efficiency

A

| Dosage, ppm | Observations | Propionate Production, mM/d | |
|---|---|---|---|
| | | Mean | Std. Dev. |
| 0 | 26 | 9.6 | 1.4 |
| 0.04 | 14 | 14.3 | 1.7 |
| 0.2 | 14 | 14.8 | 1.4 |
| 1.0 | 14 | 22.3 | 3.4 |
| 5.0 | 14 | 21.8 | 2.7 |

B

Ratio of Treated to Control Values

| Dosage mcg/mL | Molar % Propionate | Molar % Acetate | Molar % Butyrate | Total VFA mM/L |
|---|---|---|---|---|
| 1.0 | 1.532 | 0.845 | 0.754 | 0.858 |
| 2.5 | 1.459 | 0.851 | 0.827 | 0.823 |
| 5.0 | 1.562 | 0.799 | 0.839 | 0.773 |
| 10.0 | 1.709 | 0.772 | 0.728 | 0.876 |

LSD; two-tailed t-test; significant at $P < 0.01$; $C_3 > 99$ percent upper confidence limit The A80577 compounds are typically effective in increasing propionate and, thereby, improve the efficiency of feed utilization when administered to ruminants orally at rates of from about 0.01 mg/kg/day to about 1.0 mg/kg/day. Preferable rates of administration are from about 0.06 mg/kg/day to about 0.35 mg/kg/day. A preferred method of administration is to mix the compound with the animals' feed. Feed compositions adapted to increase feed utilization in ruminant animals typically comprise a feed ration and from 0.5 to 50 grams of an A80577 compound per ton of feed, preferably 2 to 15 grams per ton.

As described supra, A80577 compounds are active against anaerobic bacteria, including *Clostridium perfringens*. A80577 compounds should, therefore, be beneficial in the treatment of (which includes prevention of) enteritis in chickens, swine, cattle and sheep. A80577 compounds should also be useful in the treatment of enterotoxemia in ruminants.

The A80577 compounds can be administered to animals orally or parenterally. The most practical way to administer the A80577 compounds is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses, or capsules. Each individual dosage unit should contain a quantity of A80577 compound directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid or solid preparations.

The final formulation of feeds for animals will depend upon the amount of drug to be administered. The common methods of formulating, mixing, and pelleting feeds may be used to prepare feeds containing an A80577 compound.

The A80577 compounds may be formulated for parenteral administration by methods recognized in the veterinary pharmaceutical art. Effective injectable compositions containing the A80577 compounds may be in either suspension or solution form. In the solution form, the A80577 compound is dissolved in a physiologically acceptable carrier. Such carriers comprise a suitable solvent, preservatives such as benzyl alcohol, if needed, and buffers. Useful solvents include, for example, alcohols, glycols, or inert oils such as vegetable oils or highly refined mineral oils.

Injectable suspension compositions are prepared using a nonsolvent for the compound with adjuvants, as a carrier. The nonsolvent can be, for example, water or a glycol such as polyethylene glycol.

Suitable physiologically-acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the liquid nonsolvent can assist in making injectable suspensions in individual cases. For example, silicone antifoams, glycols, sorbitol, and sugars can be useful suspending agents.

In order to illustrate more fully the operation of this invention, the following examples are provided:

EXAMPLE 1

Preparation of Antibiotic A80577 Using *Actinomadura verrucosospora*

A. Shake-flask Fermentation of *Actinomadura verrucosospora*

The culture *Actinomadura verrucosospora*, NRRL 18236, either as a lyophilized pellet or as a suspension maintained in liquid nitrogen, is used to inoculate a vegetative medium having the following composition:

| Vegetative or Seed Medium | |
|---|---|
| Ingredient | Amount (g/L) |
| Glucose | 10.0 |
| Soluble starch | 20.0 |
| Enzyme-hydrolyzed casein* | 5.0 |
| Yeast extract | 5.0 |
| $CaCO_3$ | 1.0 |

| Vegetative or Seed Medium | |
|---|---|
| Ingredient | Amount (g/L) |
| Deionized water | q.s. 1 liter |

*N-Z Amine A, Humko-Sheffield Chemical, Norwich, NJ.

Slants or plates are prepared by adding 2.5% agar to the seed medium. The inoculated slant is incubated at 30° C. for from about 10 to about 14 days. The mature slant culture is scraped with a sterile tool to loosen the spores and remove and macerate the mycelial mat. About one-fourth of the loosened spores and culture growth thus obtained is used to inoculate 500 mL of a first-stage seed medium.

The inoculated first-stage medium is incubated in a 250-mL Erlenmeyer flask at 30° C. for about 72 hours on a shaker orbiting in a two-inch (5.08 cm) circle at This incubated first-stage medium (1.00 mL) is used to inoculate 50 mL of a production medium having the following composition:

| Ingredient | Amount (g/L) |
|---|---|
| Glucose | 25.0 |
| Blackstrap molasses | 15.0 |
| Yeast extract | 5.0 |
| Enzyme-hydrolyzed casein* | 3.0 |
| MgSO$_4$ (anhydrous) | 1.0 |
| CaCO$_3$ | 2.0 |
| Tap water | q.s. 1 liter |

*N-Z Amine A.

The inoculated production medium is incubated in a 250-mL wide-mouth Erlenmeyer flask at 30° C. for 8 to 10 days on a shaker orbiting in a two-inch circle at 250 rpm.

B. Tank Fermentation of *Actinomadura verrucosospora*

In order to provide a large volume of inoculum, 10 mL of incubated first-stage medium, prepared as described in Section A, is used to inoculate 400 mL of a second-stage growth medium having the same composition as that of the first-stage medium. This second-stage vegetative medium is incubated in a two-liter wide-mouth Erlenmeyer flask for about 48 hours at 30° C. on a shaker orbiting in a two-inch circle at 250 rpm.

Incubated second-stage vegetative medium (100 mL) thus prepared is used to inoculated 100 liters of sterile production medium, prepared as described in Section A except that P-2000 (0.1 ml/L) and Sag 471 (0.2 g/L) antifoam agents are added. The inoculated production medium is allowed to ferment in a 165-liter stirred fermentation tank for 4 to 5 days at a temperature of 30° C. The airflow (0.5–0.6 v/v/m) in the stirred vessel (200–250 rpm) is adjusted to maintain a dissolved oxygen level above 30% of air saturation.

EXAMPLE 2

Isolation of A80577 Sodium Salt

Combined fermentation broth (187 L) from two 100 L fermentations was filtered with the aid of 3% Hyflo Supercel. The mycelial filter cake was extracted twice with 40 L acetone. The acetone extracts were combined and concentrated in vacuo to remove the acetone. The concentrate (20 L) was combined with the broth filtrate (162 L), the solution was adjusted to pH 9.0 with 50% NaOH and extracted with 125 L ethyl acetate. The ethyl acetate extract was concentrated in vacuo to a residue which crystallized upon standing at 5° C. The crystals were washed sequentially with pentane, acetonitrile and diethyl ether and dried in vacuo. A yield of 36.4% grams of white crystalline A80577 sodium salt (m.p. 275°–278° C.) was obtained.

The crystals were recrystallized by dissolving to stand at 5° C. for 72 hours to crystallize. Crystallization was completed with the further addition of 100 ml of water:acetone (3:1). The crystals were filtered off and dried to yield 788 mg (m.p. 276°–278° C).

Further recovery of A80577 sodium salt from the combined above washes and mother liquor was achieved by concentrating the solution to dryness, dissolving in 250 ml toluene and applying to a column containing 2 L of silica gel Grace Grade 62) packed in toluene. The column was washed with 10 L toluene and then developed sequentially with 10 L toluene:ethanol (98:2) and 10 L toluene:ethanol (96:4) collecting 1 L fractions. The elution was followed by TLC and bioassay using *Bacillus subtilis*. Fractions 13–18 containing A80577 were combined and concentrated in vacuo to a residue which was washed with diethyl ether and dried to yield 2.3 g of amorphous A80577 Na.

EXAMPLE 3

Preparation of A80577 Free Acid

A80577 sodium salt (1 g) was dissolved in 100 ml acetone and 0.1 N Cl (100 ml) was added. The solution was stirred for 15 minutes. The solution was extracted twice with ethyl acetate (100 mL each). The ethyl acetate extracts were combined and concentrated in vacuo to an oily residue. The residue was dissolved in dioxane (50 mL) and freeze-dried to yield 0.9 g of A80577 acid.

EXAMPLE 4

Preparation of A80577 Potassium Salt

A80577 (acid form, 100 mg) was dissolved in tetrahydrofuran (20 mL). Water (3 mL) and 2N KOH (6 mL) were added and the mixture was stirred for 15 minutes. Water (30 mL) was added and the solution was extracted twice with diethyl ether (60 mL each). The combined extracts were evaporated under vacuum to dryness. The residue was dissolved in dioxane and freeze-dried to yield 100 mg of A80577 as the potassium salt (m.p. 270°–272° C.).

We claim:

1. Antibiotic A80577 which as the formula

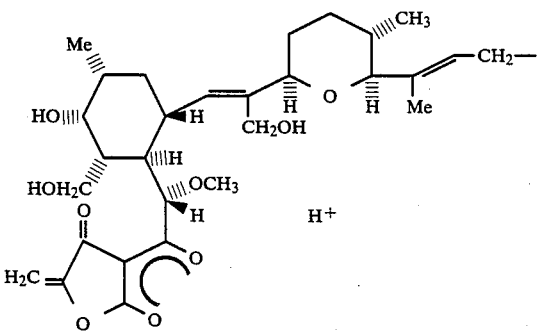

-continued

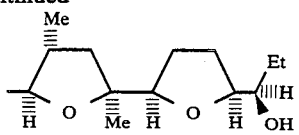

an acyl ester or alkyl ether derivative of A80577, or a salt of A80577 or of said ester or ether derivative.

2. A compound of claim 1 which is A80577, an acyl ester or alkyl ether derivative of A80577 or a pharmaceutically acceptable salt of A80577 or of said derivative.

3. A compound of claim I which is antibiotic A80577 or a salt of A80577.

4. A compound of claim 3 which is the sodium salt of A80577.

5. A compound of claim 3 which is the potassium salt of A80577.

6. A compound of claim 1 which is a $C_1$–$C_7$-acyl ester derivative of A80577 or a salt of this compound.

7. The compound of claim 4 which is the acetyl derivative of A80577.

8. The compound of claim 4 which is the propionyl derivative of A80577.

9. A process for increasing feed-utilization efficiency in a ruminant animal which comprises orally administering to the animal an effective propionate-increasing amount of a compound of claim 2.

10. The process of claim 9 wherein the compound is A80577 or a pharmaceutically acceptable salt of A80577.

11. The process of claim 9 wherein the compound is a $C_1$–$C_7$-acyl ester derivative of A80577 or a pharmaceutically acceptable salt of the derivative.

12. The process of claim 9 wherein the compound is a $C_1$–$C_4$-alkyl ether derivative of A80577 or a pharmaceutically acceptable salt of the derivative.

13. A feed composition for increasing feed utilization efficiency in ruminant animals comprising animal feed and an effective amount of a compound of claim 2.

* * * * *

UNITED STATES PATENT AND TRADEMARK OFFICE
CERTIFICATE OF CORRECTION

PATENT NO. : 4,876,273
DATED : October 24, 1989
INVENTOR(S) : Robert L. Hamill and Raymond C. Yao It is certified that error appears in the above-identified patent and that said Letters Patent is hereby corrected as shown below:

In column 1, lines 24 thru 30, and column 14, lines 61 thru 68

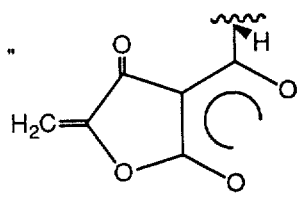 should read -- 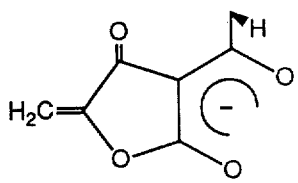 --.

In claim 3, in column 15, line 14, "claim I" should read -- claim 1 --.

Signed and Sealed this

Nineteenth Day of February, 1991

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,876,273
DATED : October 24, 1989
INVENTOR(S) : Robert L. Hamill and Raymond C. Yao It is certified that error appears in the above-identified patent and that said Letters Patent is hereby corrected as shown below:

In column 1, lines 24 thru 30, and column 14, lines 61 thru 68

Signed and Sealed this

Twentieth Day of October, 1992

*Attest:*

DOUGLAS B. COMER

*Attesting Officer*     Acting Commissioner of Patents and Trademarks